(12) United States Patent
Krishna et al.

(10) Patent No.: US 10,617,294 B1
(45) Date of Patent: Apr. 14, 2020

(54) SYSTEM AND METHOD FOR DETERMINING THE SPHERICAL POWER OF EYES BASED ON MEASURED REFRACTIVE ERROR

(71) Applicants: Viswesh Krishna, Bangalore (IN); Vrishab Krishna, Bangalore (IN)

(72) Inventors: Viswesh Krishna, Bangalore (IN); Vrishab Krishna, Bangalore (IN)

( * ) Notice: Subject to any disclaimer, the term of this patent is extended or adjusted under 35 U.S.C. 154(b) by 0 days.

(21) Appl. No.: 16/387,480

(22) Filed: Apr. 17, 2019

(30) Foreign Application Priority Data

Feb. 5, 2019 (IN) .............................. 201941004554

(51) Int. Cl.
*G06K 9/00* (2006.01)
*G06T 7/11* (2017.01)
*G06T 7/73* (2017.01)
*G06T 7/90* (2017.01)
*A61B 3/00* (2006.01)
*G06T 7/62* (2017.01)
*A61B 3/103* (2006.01)
*A61B 5/00* (2006.01)
*G16H 30/20* (2018.01)
*G06T 7/00* (2017.01)

(52) U.S. Cl.
CPC .......... *A61B 3/0025* (2013.01); *A61B 3/103* (2013.01); *A61B 5/0077* (2013.01); *A61B 5/7278* (2013.01); *G06K 9/00281* (2013.01); *G06T 7/0012* (2013.01); *G06T 7/11* (2017.01); *G06T 7/62* (2017.01); *G06T 7/73* (2017.01); *G06T 7/90* (2017.01); *G16H 30/20* (2018.01); *G06T 2207/10024* (2013.01); *G06T 2207/20132* (2013.01); *G06T 2207/30041* (2013.01); *G06T 2207/30204* (2013.01)

(58) Field of Classification Search
None
See application file for complete search history.

(56) References Cited

U.S. PATENT DOCUMENTS

2016/0171688 A1\* 6/2016 Farsiu .................. A61B 5/0066
382/131

\* cited by examiner

*Primary Examiner* — Idowu O Osifade

(57) ABSTRACT

A system for determining a spherical power of the eyes of the subject based on the measured refractive error associated with the red reflex image is provided. The system (i) predicts a position of a plurality of facial landmarks on the facial image of the subject, (ii) extracts the eyes from the facial image based on the facial landmarks, (iii) determines a position of the eyelid, (iv) determines a red reflex in the iris of the eye, (v) locates the red reflex with a reddish hue and a crescent in the iris for measuring the refractive error, (vi) generates a mask of the crescent by thresholding the red reflex image, (vii) determines a width of anti-crescent in the red reflex image, and (viii) determines a spherical power using the width of the anti-crescent, eccentricity and working distance of the image capturing device and a diameter of the pupil.

20 Claims, 5 Drawing Sheets

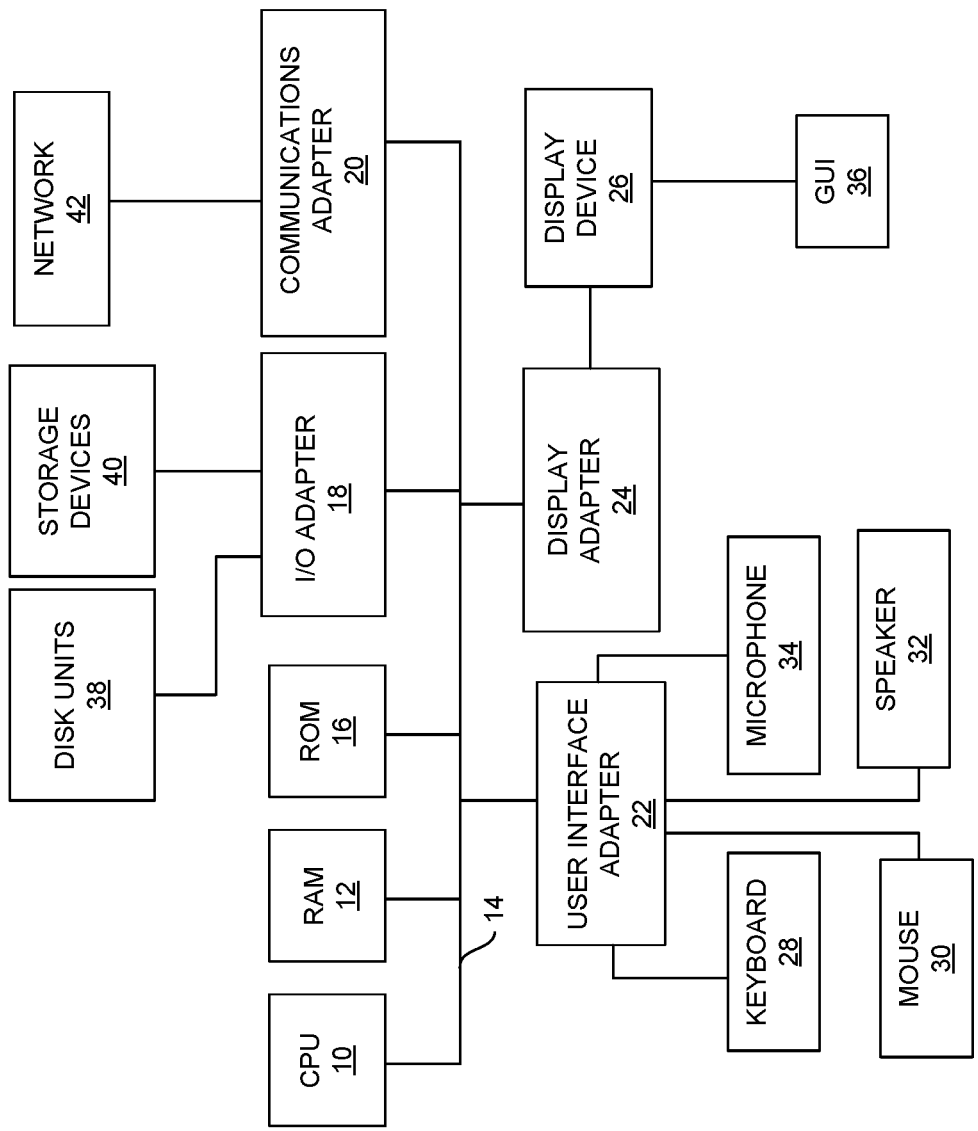

SYSTEM AND METHOD FOR DETERMINING THE SPHERICAL POWER OF EYES BASED ON MEASURED REFRACTIVE ERROR

BACKGROUND

Technical Field

The embodiments herein generally relate to a system and method for measuring a refractive error associated with eyes of a subject by analyzing an image of the face of the subject containing the red reflex (or retinoscopic reflex) associated with the image, and more specifically to a system and method for determining a spherical power of the eyes of the subject based on the measured refractive error associated with the red reflex image.

Description of the Related Art

Optometry is direcred towards improving vision, detecting abormalities and treating various eye diseases. Myopia and hyperopia are optical imperfections that occur in the eyes and these conditions are commonly detected through examination of an eye specialist such as an Optician, Optometrist or Ophthalmologist. The examination is performed based on the pupilliary red reflex test, which is carried out by passing a light through the eyes. The light reaches the transparent retina and is reflected back out of the pupil. The reflected light will be obtained as a red reflex which depends upon the blood and the amount of pigment in the oveyling layer of retina called choroid that nourishes the retina.

Generally, opticians use photorefraction devices to examine the red reflex associated with the eyes for detect optical imperfect conditions. These instruments have a higher degree of complexity and they need sophisticated arrangements. Hence as an alternative, small band-held ophthalmoscopes are being used by Ophthalmologist which are very costly and stands as a limiting factor to treat patients who are economically backward especially in developing nations. Also, rural populations have a very limited accessibility to such facilities due to economic factors and timely detection of eye defects and subsequent treatment remains a great challenge for them. Though existing approaches provide methods to measure optical imperfections using photorefraction techniques by integration with portable devices, the image processing with these methods were not very effective and are they capable of calculating only aberrations associated with the eyes.

Accordingly, there remains a need for a system and method for determining a spherical power of the eyes of the subject based on the measured refractive error associated with the red reflex image.

SUMMARY

In view of the foregoing, an embodiment herein provides a method of measuring a refractive error associated with eyes of a subject by analyzing an image of a face of the subject containing the red reflex (or retinoscopic reflex) associated with the image and determining a spherical power of the eyes of the subject based on the measured refractive error associated with the red reflex image for detecting optical imperfection conditions. The method includes the steps of: (i) generating a database with facial images associated with a subject; (ii) automatically implementing an ensemble of regression trees model, using a pose estimator as a facial landmark detection technique, to predict a position of a plurality of facial landmarks on the facial image of the subject including points on the eyelid and canthi; (iii) automatically segmenting an eye region from the facial image of the subject by identifying the eyes from the facial image based on the position of the plurality of the facial landmarks; (iv) automatically determining a position of the eyelid by estimating the eyelid shape curve in the segmented eye region; (v) automatically determining a red reflex in iris of the eye by processing the segmented eye region; (vi) measuring a refractive error by automatically identifying the red reflex with a reddish hue and a crescent in the iris; (vii) automatically generating a mask of the crescent by thresholding the red reflex image using an Otsu's binary thresholding technique; (viii) automatically determining a width of anti-crescent in the red reflex image using a number of white pixels in the mask; and (ix) automatically determining a spherical power using the width of the anti-crescent, eccentricity of the image capturing device, a working distance of the image capturing device and a diameter of the pupil.

In some embodiments, the facial image is captured using an image capturing device.

In some embodiments, the eyelid shape curve refers to a contour of a junction of the eyelid with the eye.

In some embodiments, the refractive error is measured by thresholding the red reflex images using a red channel of the RGB image and calculating an average red value as a global threshold.

In some embodiments, the crescent comprises a segment of a circular pupil.

In some embodiments, the determination of the red reflex in the iris of the eye includes the steps of: (a) automatically estimating an average lightness value of all the pixels in an eye bounding box associated with the iris of the eye; (b) automatically identifying a plurality of iris shades in the eye by classifying an angle representing hue; (c) automatically segmenting, using a sliding-window algorithm, the iris as the region with the highest concentration of dark-colored pixels; and (d) automatically trimming the iris region of the image based on the red channel in the eye to obtain the red reflex image of the iris.

In some embodiments, the angle representing hue is classified by comparing against various thresholds.

In some embodiments, the dark-colored pixels are determined based on the estimated average lightness value of the pixels.

In some embodiments, the pose detector is trained using a machine learning model and the machine learning model comprise techniques employed in Digital object detection Library (Dlib).

In some embodiments, the facial landmark detection technique identifies frontal human faces in the facial image and estimates their pose with 50 to 200 landmarks on the face of the subject.

In some embodiments, the facial landmark detection technique comprises at least one of the Histogram of Ordered Gradients (HOG) feature combining with a linear classifier, an image pyramid and sliding window detection.

In some embodiments, the positions of the facial landmarks are indexed from 37-42 for the right eye and 43-48 for the left eye to identify the eyes from the facial image of the subject.

In some embodiments, the eyelid shape curve is fitted to an approximation function comprising at least one of quadratic, cubic, or ellipsoidal shapes. In some embodiments, the estimation of the eyelid shape curvature can determine a level of blepharoptosis of the subject.

In some embodiments, the average lightness value of all the pixels in the eye bounding box is multiplied by a suitable constant factor to threshold the image as a global threshold.

In some embodiments, the center of the iris is a geometrical center of the eye bounding box. In some embodiments, a radius of the iris is a width of the eye bounding box of the iris.

In some embodiments, the angle at which the segment subtends at the center of the crescent is estimated using a Linear Approximation.

In some embodiments, the eccentricity of the image capturing device is defined to be the distance between the nearest edge of the camera lens and the center of the flash in the image capturing device.

In some embodiments, the working distance is estimated using the iris and its width as a marker which is scaled by a ratio dependent on resolution of the image capturing device.

In some embodiments, the facial image of the subject image is preprocessed for noise removal, contrast improvements and blur detection.

In some embodiments, the noise removal of the facial image is performed by smoothing the facial image using Gaussian blurring.

In some embodiments, the contrast improvements of the facial image include applying a gamma correction with a suitable value depending on the average pixel value.

In some embodiments, the blur detection in the facial image is performed using a variance of the Laplacian of Gaussian (LoG) operation.

In one aspect, one or more non-transitory computer readable storage mediums storing instructions, which when executed by a processor, performs a method for automatically analysing an image of a face of the subject containing the red reflex (or retinoscopic reflex) associated with the image, measurement of a refractive error associated with eyes of a subject, and determination of a spherical power of the eyes of the subject based on the measured refractive error is provided. The method includes steps of: (i) generating a database with facial images associated with a subject; (ii) automatically implementing an ensemble of regression trees model, using a pose estimator as a facial landmark detection technique, to predict a position of a plurality of facial landmarks on the facial image of the subject including points on the eyelid and canthi; (iii) automatically segmenting an eye region from the facial image of the subject by identifying the eyes from the facial image based on the position of the plurality of the facial landmarks, (iv) automatically determining a position of the eyelid by estimating the eyelid shape curve in the segmented eye region; (v) automatically determining a red reflex in the iris of the eye by processing the segmented eye region; (vi) measuring a refractive error by automatically identifying the red reflex with a reddish hue and a crescent in the iris; (vii) automatically generating a mask of the crescent by thresholding the red reflex image using an Otsu's binary thresholding technique; (viii) automatically determining a width of anti-crescent in the red reflex image using a number of white pixels in the mask; and (ix) automatically determining a spherical power using the width of the anti-crescent, eccentricity of the image capturing device, a working distance of the image capturing device and a diameter of the pupil.

In some embodiments, the facial image is captured using an image capturing device.

In some embodiments, the eyelid shape curve refers to a contour of a junction of the eyelid with the eye.

In some embodiments, the refractive error is measured by thresholding the red reflex images using a red channel of the RGB image and calculating an average red value as a global threshold.

In, some embodiments, the crescent comprises a segment of a circular pupil.

In some embodiments, the determination of the red reflex in the iris of the eye includes the steps of: (a) automatically estimating an average lightness value of all the pixels in an eye bounding box associated with the iris of the eye; (b) automatically identifying a plurality of iris shades in the eye by classifying an angle representing hue; (c) automatically segmenting, using a sliding-window algorithm, the iris as the region with the highest concentration of dark-colored pixels; and (d) automatically trimming the iris region of the image based on the red channel in the eye to obtain the red reflex image of the iris.

In some embodiments, the angle representing hue is classified by comparing against various thresholds.

In some embodiments, the dark-colored pixels are determined based on the estimated average lightness value of the pixels.

In some embodiments, the pose detector is trained using a machine learning model and the machine learning model comprise techniques employed in Digital object detection Library (Dlib).

In some embodiments, the facial landmark detection technique identifies frontal human faces in the facial image and estimates their pose with 50 to 200 landmarks on the face of the subject.

In some embodiments, the facial landmark detection technique comprises at least one of the Histogram of Ordered Gradients (HOG) feature combining with a linear classifier, an image pyramid and sliding window detection.

In some embodiments, the positions of the facial landmarks are indexed from 37-42 for the right eye and 43-48 for the left eye to identify the eyes from the facial image of the subject.

In some embodiments, the eyelid shape curve is fitted to an approximation function comprising at least one of quadratic, cubic, or ellipsoidal shapes. In some embodiments, the estimation of the eyelid shape curvature can determine a level of blepharoptosis of the subject.

In some embodiments, the average lightness value of all the pixels in the eye bounding box is multiplied by a suitable constant factor to threshold the image as a global threshold.

In some embodiments, the center of the iris is a geometrical center of the eye bounding box. In some embodiments, a radius of the iris is a width of the eye bounding box of the iris.

In some embodiments, the angle at which the segment subtends at the center of the crescent is estimated using a Linear Approximation.

In some embodiments, the eccentricity of the image capturing device is defined to be the distance between the nearest edge of the camera lens and the center of the flash in the image capturing device.

In some embodiments, the working distance is estimated using the iris and its width as a marker which is scaled by a ratio dependent on resolution of the image capturing device.

In some embodiments, the facial image of the subject image is preprocessed for noise removal, contrast improvements and blur detection.

In some embodiments, the noise removal of the facial image is performed by smoothing the facial image using Gaussian blurring.

In some embodiments, the contrast improvements of the facial image include applying a gamma correction with a suitable value depending on the average pixel value.

In some embodiments, the blur detection in the facial image is performed using a variance of the Laplacian of Gaussian (LoG) operation.

In another aspect, a system for automatically analyzing an image of a face of the subject containing the red reflex (or retinoscopic reflex) associated with the image, measuring a refractive error associated with eyes of a subject, and determining a spherical power of the eyes of the subject based on the measured refractive error associated with the red reflex image for detecting optical imperfection conditions is provided. The system includes a memory, and a device processor. The memory includes a database that stores facial images associated with the subject. The facial image is captured using an image capturing device. The database stores one or more modules executable by the device processor. The set of modules includes (i) a database generation module that generates a database with facial images associated with a subject; (ii) a pose prediction module that predict a position of a plurality of facial landmarks on the facial image of the subject including points on the eyelid and canthi; (iii) an eye extraction module that segments an eye region from the facial image of the subject by identifying the eyes based on the position of the plurality of the facial landmarks; (iv) an eyelid position determination module that determining a position of the eyelid by estimating the eyelid shape curve in the segmented eye region; (v) a red reflex determination module that determines a red reflex in iris of the eye by processing the segmented eye region; (vi) a refractive error measurement module that automatically identifies the red reflex with a reddish hue and a crescent in the iris; (vii) a mask generation module that generates a mask of the crescent by thresholding the red reflex image using an Otsu's binary thresholding technique; (viii) an anti-crescent width determination module that determines a width of anti-crescent in the red reflex image using a number of white pixels in the mask; and (ix) a spherical power determination module that determines a spherical power using the width of the anti-crescent, eccentricity of the image capturing device, a working distance of the image capturing device and a diameter of the pupil.

In some embodiments, the facial image is captured using an image capturing device. In some embodiments, the pose prediction module implements an ensemble of regression trees model using a pose estimator as a facial landmark detection technique. In some embodiments, the eyelid shape curve refers to a contour of a junction of the eyelid with the eye. In some embodiments, the refractive error is measured by thresholding the red reflex images using a red channel of the RGB image and calculating an average red value as a global threshold. In some embodiments, the crescent comprises a segment of a circular pupil.

In some embodiments, the determination of the red reflex in the iris of the eye includes the steps of: (a) automatically estimating an average lightness value of all the pixels in an eye bounding box associated with the iris of the eye; (b) automatically identifying a plurality of iris shades in the eye by classifying an angle representing hue; (c) automatically segmenting, using a sliding-window algorithm, the iris as the region with the highest concentration of dark-colored pixels; and (d) automatically trimming the iris region of the image based on the red channel in the eye to obtain the red reflex image of the iris.

In some embodiments, the angle representing hue is classified by comparing against various thresholds.

In some embodiments, the dark-colored pixels are determined based on the estimated average lightness value of the pixels.

In some embodiments, the pose detector is trained using a machine learning model and the machine learning model comprise techniques employed in Digital object detection Library (Dlib).

In some embodiments, the facial landmark detection technique identifies frontal human faces in the facial image and estimates their pose with 50 to 200 landmarks on the face of the subject.

In some embodiments, the facial landmark detection technique comprises at least one of the Histogram of Ordered Gradients (HOG) feature combining with a linear classifier, an image pyramid and sliding window detection.

In some embodiments, the positions of the facial landmarks are indexed from 37-42 for the right eye and 43-48 for the left eye to identify the eyes from the facial image of the subject.

In some embodiments, the eyelid shape curve is fitted to an approximation function comprising at least one of quadratic, cubic, or ellipsoidal shapes. In some embodiments, the estimation of the eyelid shape curvature can determine a level of blepharoptosis of the subject.

In some embodiments, the average lightness value of all the pixels in the eye bounding box is multiplied by a suitable constant factor to threshold the image as a global threshold.

In some embodiments, the center of the iris is a geometrical center of the eye bounding box. In some embodiments, a radius of the iris is a width of the eye bounding box of the iris.

In some embodiments, the angle at which the segment subtends at the center of the crescent is estimated using a Linear Approximation.

In some embodiments, the eccentricity of the image capturing device is defined to be the distance between the nearest edge of the camera lens and the center of the flash in the image capturing device.

In some embodiments, the working distance is estimated using the iris and its width as a marker which is scaled by a ratio dependent on resolution of the image capturing device.

In some embodiments, the facial image of the subject image is preprocessed for noise removal, contrast improvements and blur detection.

In some embodiments, the noise removal of the facial image is performed by smoothing the facial image using Gaussian blurring.

In some embodiments, the contrast improvements of the facial image include applying a gamma correction with a suitable value depending on the average pixel value.

In some embodiments, the blur detection in the facial image is performed using a variance of the Laplacian of Gaussian (LoG) operation.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 4 is a schematic diagram of a computer architecture in accordance with the embodiments herein.

DETAILED DESCRIPTION OF THE DRAWINGS

Figure 1:
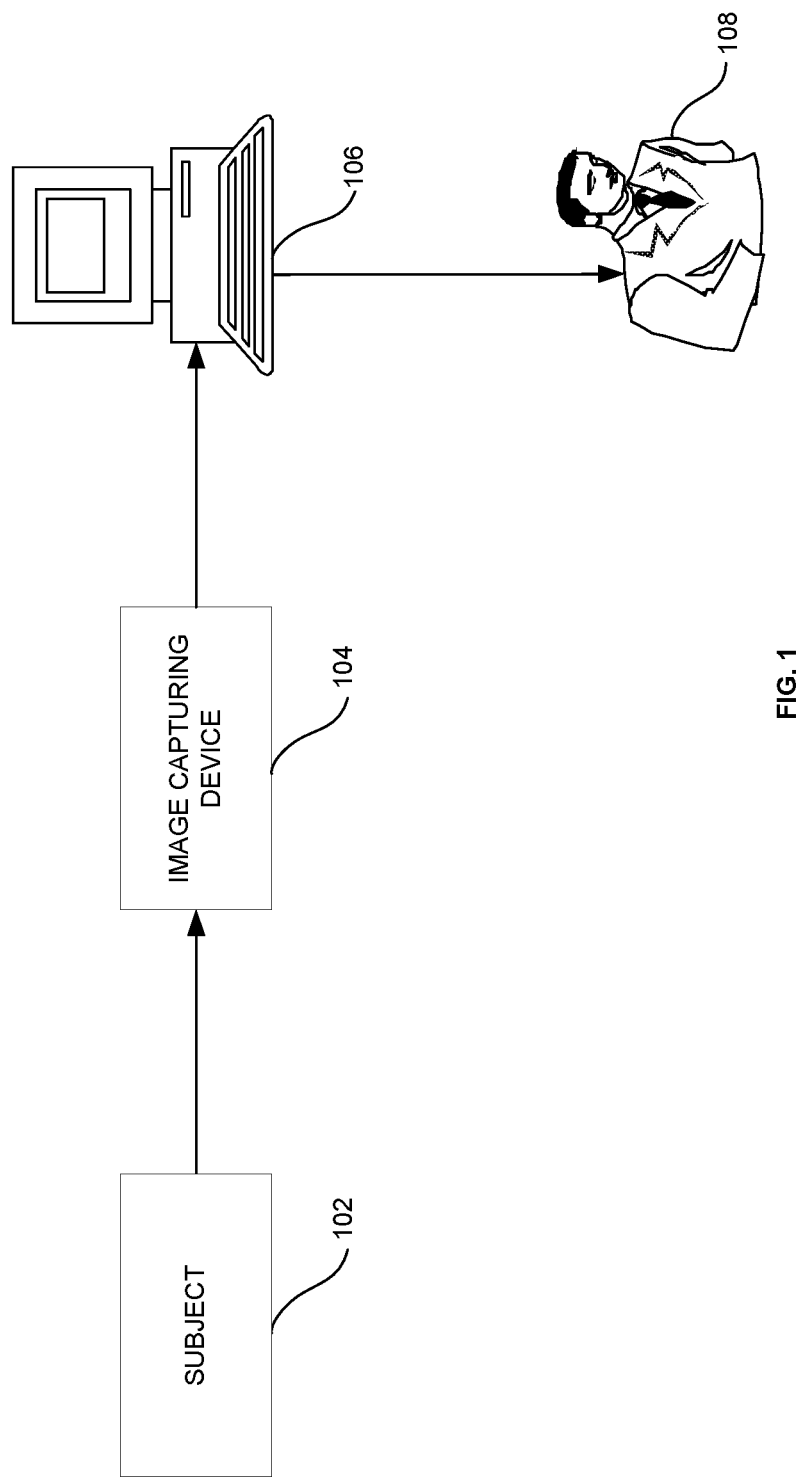
FIG. 1 illustrates a system view of a spherical power determination system for determining a spherical power of the eyes of the subject based on measured refractive error associated with a red reflex image according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various embodiments disclosed herein provide a system and a method for. Referring now to the drawings, and more particularly to FIGS. 1 through 4, where determining a spherical power of the eyes of the subject based on the measured refractive error associated with the red reflex image similar reference characters denote corresponding features consistently throughout the figures, preferred embodiments are shown.

FIG. 1 illustrates a system view of a spherical power determination system for determining a spherical power of the eyes of the subject based on measured refractive error associated with a red reflex image according to an embodiment herein. The system view includes a subject 102, an image capturing device 104, the spherical power determination system 106 and the user 108. The image capturing device 104 obtains a facial image of the subject 102. The spherical power determination system 106 is communicatively connected to the image capturing device 104. The spherical power determination system 106 provides a spherical power associated with the eyes of the subject 102 to a user 108. In one embodiment, the spherical power determination system 106 may be a mobile phone, a kindle, a PDA (Personal Digital Assistant), a tablet, a music player, a computer, an electronic notebook or a smartphone. The spherical power determination system 106 includes a memory and a processor. The image capturing device 104 captures a facial image of the subject 102. The spherical power determination system 106 generates a database of facial images associated with a subject 102. The spherical power determination system 106 predicts a position of a plurality of facial landmarks on the facial image of the subject including points on the eyelid and canthi using a pose estimator implementing an ensemble of regression trees model as a facial landmark detection technique. The spherical power determination system 106 extracts the eyes from the facial image of the subject by identifying the eyes based on the position of the plurality of the facial landmarks. The spherical power determination system 106 determines a position of the eyelid by estimating the eyelid shape curve. The eyelid shape curve refers to a contour of a junction of the eyelid with the eye. The spherical power determination system 106 determining a red reflex in the iris of the eye. The spherical power determination system 106 locates the red reflex with a reddish hue and a crescent in the iris for measuring the refractive error. The refractive error is measured by thresholding the red reflex images using a red channel of the RGB image and calculating an average red value as a global threshold. The spherical power determination system 106 generates a mask of the crescent by thresholding the red reflex image using an. Otsu's binary thresholding technique. The crescent comprises a segment of a circular pupil. The spherical power determination system 106 determines a width of anti-crescent in the red reflex image using a number of white pixels in the mask. The spherical power determination system 106 determines a spherical power using the width of the anti-crescent, eccentricity of the image capturing device 104, a working distance of the image capturing device 104 and a diameter of the pupil.

In an embodiment, the red reflex in the iris of the eye is determined by: (a) automatically estimating an average lightness value of all the pixels in an eye bounding box associated with the iris of the eye, (b) automatically identifying a plurality of iris shades in the eye by classifying an angle representing hue, (c) automatically segmenting, using a sliding-window algorithm, the iris as the region with the highest concentration of dark-colored pixels, and (d) automatically trimming the iris region of the image based on the red channel in the eye to obtain the red reflex image of the iris. In an embodiment, the angle representing hue is classified by comparing against various thresholds. In an embodiment, the dark-colored pixels are determined based on the estimated average lightness value of the pixels;

In an embodiment, the pose detector is trained using a machine learning model and the machine learning model comprise techniques employed in Digital object detection Library (Dlib).

In an embodiment, the machine learning model is a machine learning technique that is designed to recognize and interpret the data through a machine perception, a labeling and by clustering the raw data. The machine learning model is trained to interpret the raw data by providing a collection of data as an input. The machine learning model is trained to perform the task with the processor.

Figure 2:
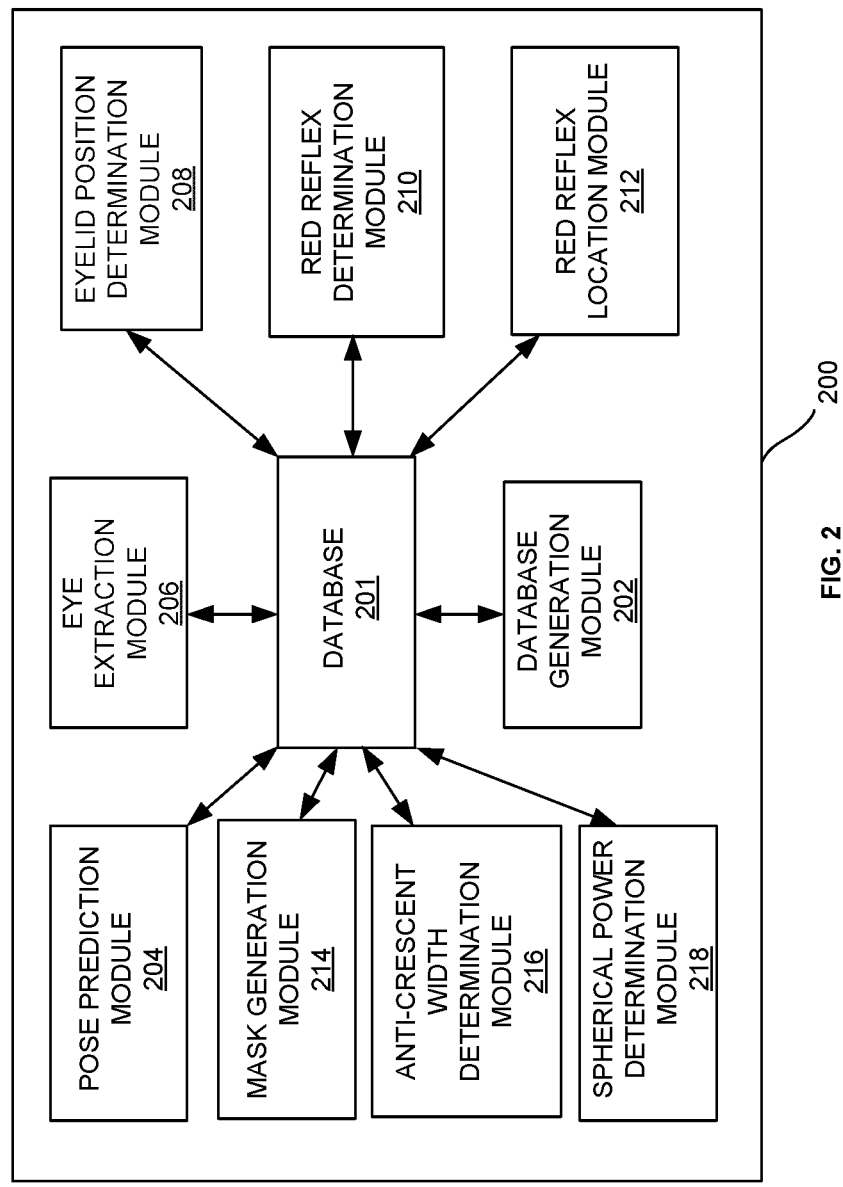
FIG. 2 is an exploded view of the spherical power determination system of FIG. 1 according to an embodiment herein.

FIG. 2 is an exploded view of the spherical power determination system of FIG. 1 according to an embodiment herein. The spherical power determination system 106 includes a database 201, a database generation module 202, a pose prediction module 204, an eye extraction module 206, an eyelid position determination module 208, a red reflex determination module 210, a red reflex location module 212, a mask generation module 214, an anti-crescent width determination module 216 and a spherical power determination module 218. The spherical power determination system 106 receives a facial image of the subject 102 to analyze the image containing the red reflex (or retinoscopic reflex) associated with the image. The facial images may be stored in the database 201 of a memory. The database generation module 202 generates the database 201 with facial images associated with the subject 102. In an embodiment, the facial images are captured using an image capturing device 104. The pose prediction module 204 predict a position of a plurality of facial landmarks on the facial image of the subject 102 including points on the eyelid and canthi. The pose prediction module 204 implements an ensemble of regression trees model using a pose estimator as a facial landmark detection technique to predict the position of a plurality of facial landmarks on the facial image of the subject 102.

An eye extraction module 206 extracts the eyes from the facial image of the subject 102 by identifying the eyes based on the position of the plurality of the facial landmarks. The eyelid position determination module 208 determines a position of the eyelid by estimating the eyelid shape curve. In an embodiment, the eyelid shape curve refers to a contour of a junction of the eyelid with the eye. The red reflex determination module 210 determines a red reflex in the iris of the eye. The red reflex location module 212 locates the red reflex with a reddish hue and a crescent in the iris for measuring the refractive error. In an embodiment, the refractive error is measured by thresholding the red reflex images using a red channel of the RGB image and calculating an average red value as a global threshold. The mask generation module 214 generates a mask of the crescent by thresholding the red reflex image using an Otsu's binary thresholding technique. In an embodiment, the crescent comprises a segment of a circular pupil. The anti-crescent width determination module 216 determines a width of anti-crescent in the red reflex image using a number of white pixels in the mask. The spherical power determination module 218 determines the spherical power associated with the eyes of the subject 102 by using (a) width of the anti-crescent, (b) eccentricity of the image capturing device, (c) a working distance of the image capturing device and (d) a diameter of the pupil.

In an embodiment, the pose prediction module 204 including the pose detector is trained using a machine learning model. In an embodiment, the machine learning model comprise techniques employed in Digital object detection Library (Dlib). In an embodiment, the facial landmark detection technique identifies frontal human faces in the facial image and estimates their pose with 50 to 200 landmarks on the face of the subject. In an embodiment, the facial landmark detection technique comprises at least one of the Histogram of Ordered Gradients (HOG) feature combining with a linear classifier, an image pyramid and sliding window detection. In an embodiment, the positions of the facial landmarks are indexed from 37-42 for the right eye and 43-48 for the left eye to identify the eyes from the facial image of the subject. In an embodiment, the eyelid position determination module 208 determining the eyelid shape curve is fitted to an approximation function comprising at least one of quadratic, cubic, or ellipsoidal shapes. In an embodiment, the estimation of the eyelid shape curvature can determine a level of blepharoptosis of the subject. In an embodiment, the red reflex determination module 210 determines the red reflex in the iris of the eye by (a) automatically estimating an average lightness value of all the pixels in an eye bounding box associated with the iris of the eye; (b) automatically identifying a plurality of iris shades in the eye by classifying an angle representing hue; (c) automatically segmenting, using a sliding-window algorithm, the iris as the region with the highest concentration of dark-colored pixels; and (d) automatically trimming the iris region of the image based on the red channel in the eye to obtain the red reflex image of the iris. In an embodiment, the angle representing hue is classified by comparing against various thresholds. In an embodiment, the dark-colored pixels are determined based on the estimated average lightness value of the pixels. In an embodiment, the iris of the eye and consequently the dimensions of the bounding box is approximated to the height of the eye. In an embodiment, the center of the iris is considered to be the geometrical center of the eye bounding box. In an embodiment, radius of the iris is a width of the eye bounding box of the iris. In an embodiment, the average lightness value of all the pixels in the eye bounding box is multiplied by a suitable constant factor to threshold the image as a global threshold. In an embodiment, the red reflex is determined from the image obtained in low light condition of 3 lumens (±2 lm).

In an embodiment, the mask generation module 214 generates the mask including the Corneal Light Reflex (CLR), which is the white dot in the pupil, if the crescent is smaller. In an embodiment, contours are extracted and those contours that are at a large distance (⅕ of the width or height) from any of the edges are eliminated while generating the mask for smaller crescent. In an embodiment, the angle at which the segment subtends at the center of the crescent is estimated using a Linear Approximation by the initial conditions:

$$a = \frac{2A}{r^2}$$

where, A is the number of white pixels in the mask and T is the radius of the pupil determined from the size of the mask.

$$\theta_0 = a$$

And recursive formula:

$$\theta_{n+1} = \theta_n + \frac{a - (\theta_n - \sin\theta_n)}{1 - \cos\theta_n}$$

The recurrence is calculated until the condition $a-(\theta_n-\sin\theta_n) \leq 10^{-3}$ is true.

In an embodiment, from the final angle θ, the width of the anti-crescent, ω, is described by the formula:

$$\omega = r(1+\cos\theta).$$

In an embodiment, the eccentricity of the image capturing device is defined to be the distance between the nearest edge of the camera lens and the center of the flash in the image capturing device. In an embodiment, the working distance is estimated using the iris and its width as a marker which is scaled by a ratio dependent on resolution of the image capturing device. In an embodiment, the spherical power of the eye using the given formula:

$$P = \frac{e}{d}\left(\frac{1}{w} - \frac{1}{2r}\right)$$

where, e is the the eccentricity of the image capturing device, ω is the anti-crescent width and d is the working distance and 2r is the diameter of the pupil. In an embodiment, the difference in power of the eyes (anisometropia), δ, is calculated by:

$$\delta = \frac{e}{d}\left(\frac{1}{w_1} - \frac{1}{w_2}\right)$$

where e is the eccentricity of the camera equipment, d is the working distance, $\omega_1$ is the anti-crescent width of the first eye and $\omega_2$ is that of the second eye.

In an embodiment, the facial image of the subject is preprocessed for noise removal, contrast improvements and blur detection. In an embodiment, the noise removal of the facial image is performed by smoothing the facial image using Gaussian blurring. In an embodiment, the contrast improvements of the facial image include applying a gamma correction with a suitable value depending on the average pixel value. In an embodiment, the blur detection in the facial image is performed using a variance of the Laplacian of Gaussian (LoG) operation.

Figure 3A:
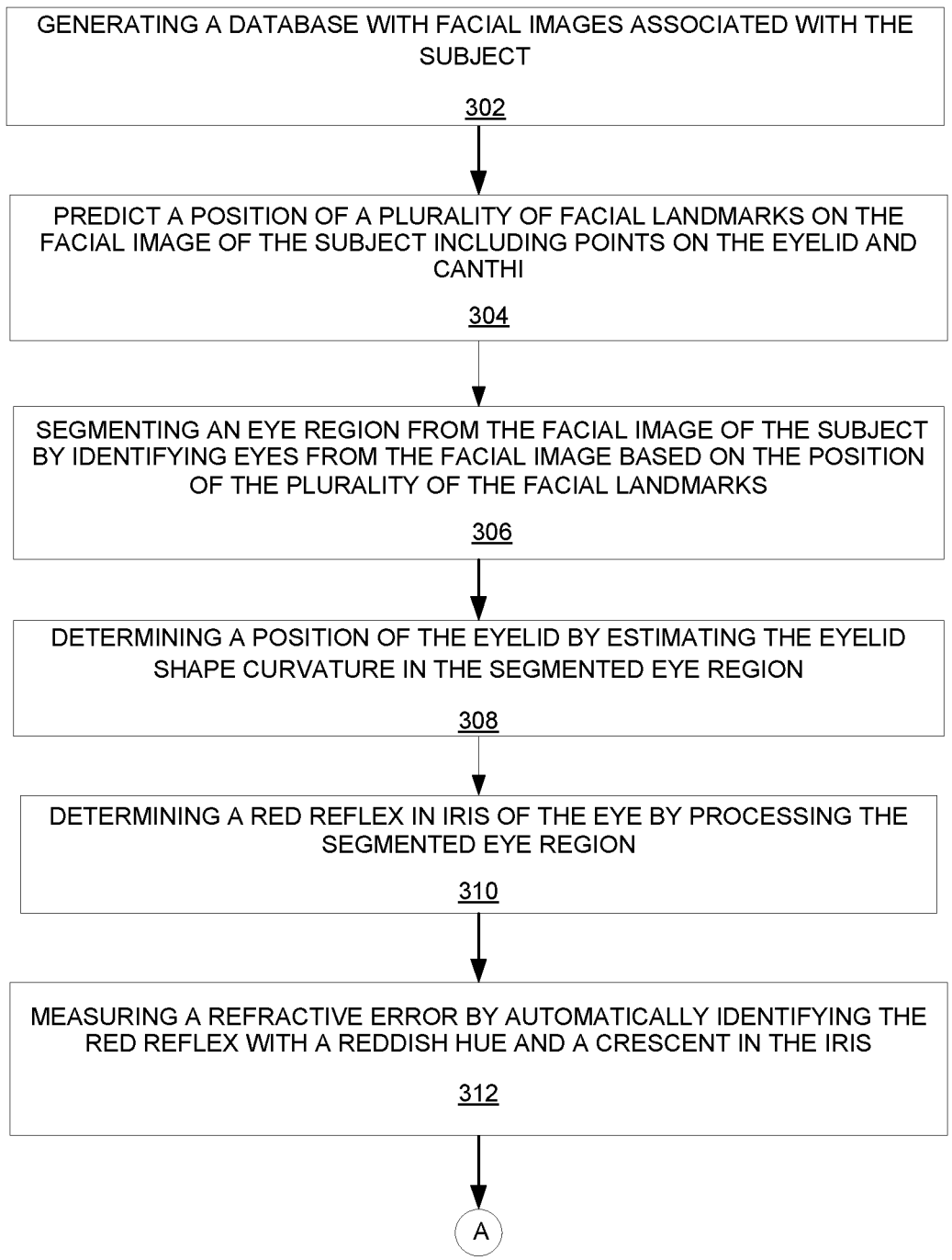
FIG. 3A and FIG. 3B are flow diagrams that illustrates a method for determining a spherical power of the eyes of the subject based on the measured refractive error associated with the red reflex image of spherical power determination system of FIG. 1 according to an embodiment herein.
Figure 3B:
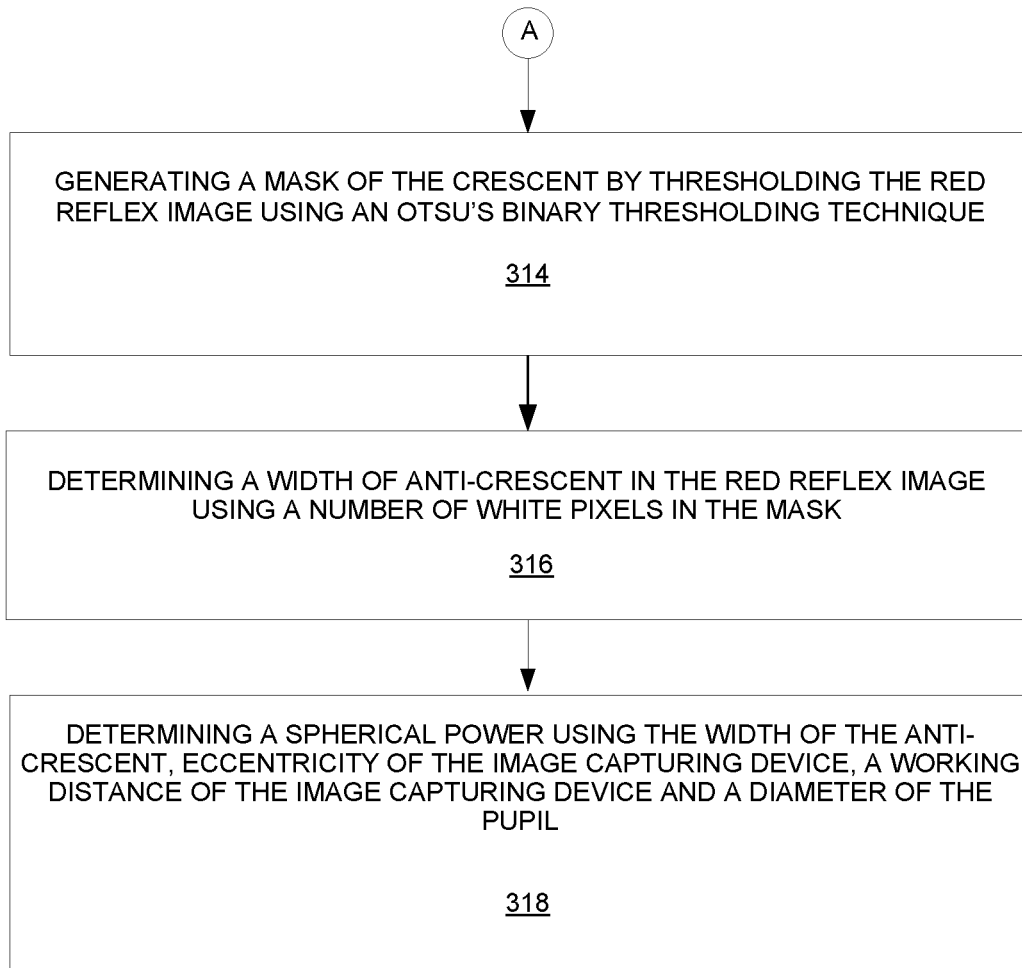

FIG. 3A and FIG. 3B are flow diagrams that illustrates a method for determining a spherical power of the eyes of the subject based on the measured refractive error associated with the red reflex image of spherical power determination system of FIG. 1 according to an embodiment herein. At step 302, a database of facial images associated with a subject is generated. At step 304, a position of a plurality of facial landmarks on the facial image of the subject including points on the eyelid and canthi is determined using a pose estimator. At step 306, the eyes from the facial image of the subject are extracted by identifying the eyes based on the position of the plurality of the facial landmarks. At step 308, a position of the eyelid is determined by estimating the eyelid shape curve. At step 310, a red reflex in the iris of the eye is determined. At step 312, the red reflex with a reddish hue and a crescent in the iris for measuring the refractive error is located. At step 314, a mask of the crescent is generated by thresholding the red reflex image using an Otsu's binary thresholding technique. Otsu's method employs a cluster based thresholding of an image to generate a mask of selected areas of interest of the image. The red reflex image is thresholded by converting the red reflex image into a binary image and the mask of the crescent is generated. At step 316, a width of anti-crescent in the red reflex image is determined using a number of white pixels in the mask. At step 318, a spherical power using the width of the anti-crescent, eccentricity of the image capturing device, a working distance of the image capturing device and a diameter of the pupil is determined.

In an embodiment, the facial image is captured using an image capturing device. In an embodiment, the pose estimator implements a an ensemble of regression trees model as a facial landmark detection technique as this model increases the predictive performance by means of weighted combination of multiple regression trees. The trees are trained over a dataset of images with annotations on the correct positions of landmark points. This technique utilize pixel intensities differences to directly estimate the landmark positions. These estimated positions are subsequently refined with an iterative process done by a cascade of regressors. The regressors produces a new estimate from the previous one, trying to reduce the alignment error of the estimated points at each iteration. In an embodiment, the eyelid shape curve refers to a contour of a junction of the eyelid with the eye. In an embodiment, the refractive error is measured by thresholding the red reflex images using a red channel of the RGB image and calculating an average red value as a global threshold. In an embodiment, the crescent comprises a segment of a circular pupil. In an embodiment, the red reflex in the iris of the eye is determined by: (a) automatically estimating an average lightness value of all the pixels in an eye bounding box associated with the iris of the eye; (b) automatically identifying a plurality of iris shades in the eye by classifying an angle representing hue; (c) automatically segmenting, using a sliding-window algorithm, the iris as the region with the highest concentration of dark-colored pixels; and (d) automatically trimming the iris region of the image based on the red channel in the eye to obtain the red reflex image of the iris. In an embodiment, the angle representing hue is classified by comparing against various thresholds. In an embodiment, the dark-colored pixels are determined based on the estimated average lightness value of the pixels.

A representative hardware environment for practicing the embodiments herein is depicted in FIG. 4, with reference to FIGS. 1 through 3. This schematic drawing illustrates a hardware configuration of a server/computer system/computing device in accordance with the embodiments herein. The system includes at least one processing device CPU 10 that may be interconnected via system bus 14 to various devices such as a random access memory (RAM) 12, read-only memory (ROM) 16, and an input/output (I/O) adapter 18. The I/O adapter 18 can connect to peripheral devices, such as disk units 38 and program storage devices 40 that are readable by the system. The system can read the inventive instructions on the program storage devices 40 and follow these instructions to execute the methodology of the embodiments herein. The system further includes a user interface adapter 22 that connects a keyboard 28, mouse 30, speaker 32, microphone 34, and/or other user interface devices such as a touch screen device (not shown) to the bus 14 to gather user input. Additionally, a communication adapter 20 connects the bus 14 to a data processing network 42, and a display adapter 24 connects the bus 14 to a display device 26, which provides a graphical user interface (GUI) 36 of the output data in accordance with the embodiments herein, or which may be embodied as an output device such as a monitor, printer, or transmitter, for example.

The foregoing description of the specific embodiments will so fully reveal the general nature of the embodiments herein that others can, by applying current knowledge, readily modify and/or adapt for various applications without departing from the generic concept, and, therefore, such adaptations and modifications should be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

We claim:

1. A method of measuring a refractive error associated with eyes of a subject by analyzing an image of a face of the subject containing the red reflex or retinoscopic reflex associated with the image and determining a spherical power of the eyes of the subject based on the measured refractive error associated with the red reflex image for detecting optical imperfection conditions, wherein the method comprising:

generating a database with a facial image associated with a subject, wherein the facial image is captured using an image capturing device;

automatically implementing an ensemble of regression trees model, using a facial landmark detection technique, to predict a position of a plurality of facial landmarks on the facial image of the subject including points on the eyelid and canthi;

automatically segmenting an eye region from the facial image of the subject by identifying eyes from the facial image based on the position of the plurality of the facial landmarks;

automatically determining a position of the eyelid by estimating the eyelid shape curve in the segmented eye region, wherein the eyelid shape curve refers to a contour of a junction of the eyelid with the eye;

automatically determining a red reflex in iris of the eye by processing the segmented eye region;

measuring a refractive error by automatically identifying the red reflex with a reddish hue and a crescent in the iris, wherein the refractive error is measured by thresholding the red reflex images using a red channel of the RGB image and calculating an average red value as a threshold value;

automatically generating a mask of the crescent by thresholding the red reflex image using an Otsu's binary thresholding technique, wherein the crescent comprises a segment of a circular pupil;

automatically determining a width of anti-crescent in the red reflex image using a number of white pixels in the mask;

automatically determining a spherical power using the width of the anti-crescent, eccentricity of the image capturing device, a working distance of the image capturing device and a diameter of the pupil.

2. The method of claim 1, wherein automatic determination of the red reflex in the iris of the eye comprising the steps of:

automatically estimating an average lightness value of all the pixels in an eye bounding box associated with the iris of the eye;

automatically identifying a plurality of iris shades in the eye by classifying an angle representing hue, wherein the angle representing hue is classified by comparing against various thresholds;

automatically segmenting, using a sliding-window algorithm, the iris as the region with the highest concentration of dark-colored pixels, wherein the dark-colored pixels are determined based on the estimated average lightness value of the pixels; and automatically trimming the iris region of the image based on the red channel in the eye to obtain the red reflex image of the iris.

3. The method of claim 1, wherein the position of the plurality of facial landmarks on the facial image of the subject is predicted using a machine learning model and the machine learning model comprises techniques that are employed in Digital object detection Library (Dlib).

4. The method of claim 1, wherein the facial landmark detection technique identifies frontal human faces in the facial image and estimates their pose with 50 to 200 landmarks on the face of the subject.

5. The method of claim 1, wherein the facial landmark detection technique comprises at least one of the Histogram of Ordered Gradients (HOG) feature combining with a linear classifier algorithm, an image pyramid technique or sliding window detection technique.

6. The method of claim 1, wherein the positions of the facial landmarks are indexed from 37-42 for the right eye and 43-48 for the left eye to identify the eyes from the facial image of the subject.

7. The method of claim 1, wherein the eyelid shape curve is fitted to an approximation function comprising at least one of quadratic, cubic, or ellipsoidal shapes, wherein the estimation of the eyelid shape curvature determines a level of blepharoptosis of the subject.

8. The method of claim 1, wherein the average lightness value of all the pixels in the eye bounding box is multiplied by a suitable constant factor to threshold the image as a global threshold.

9. The method of claim 1, wherein the center of the iris is a geometrical center of the eye bounding box, wherein a radius of the iris is a width of the eye bounding box of the iris.

10. The method of claim 1, wherein the angle at which the segment subtends at the center of the crescent is estimated using a Linear Approximation.

11. The method of claim 1, wherein the eccentricity of the image capturing device is defined to be the distance between the nearest edge of the camera lens and the center of the flash in the image capturing device.

12. The method of claim 1, wherein the working distance is estimated using the iris and its width as a marker which is scaled by a ratio dependent on resolution of the image capturing device.

13. The method of claim 1, wherein the facial image of the subject image is preprocessed for noise removal, contrast improvements and blur detection.

14. The method of claim 13, wherein the noise removal of the facial image is performed by smoothing the facial image using Gaussian blurring.

15. The method of claim 13, wherein the contrast improvements of the facial image include applying a gamma correction with a suitable value depending on the average pixel value.

16. The method of claim 13, wherein the blur detection in the facial image is performed using a variance of the Laplacian of Gaussian (LoG) operation.

17. One or more non-transitory computer readable storage mediums storing instructions, which when executed by a processor, causes automatic analysis of an image of the face of the subject containing the red reflex (or retinoscopic reflex) associated with the image, measurement of a refractive error associated with eyes of a subject, and determination of a spherical power of the eyes of the subject based on the measured refractive error associated with the red reflex image for detecting optical imperfection conditions, by performing the steps of:

generating a database with a facial image associated with a subject, wherein the facial image is captured using an image capturing device;

automatically implementing an ensemble of regression trees model, using a facial landmark detection technique, to predict a position of a plurality of facial landmarks on the facial image of the subject including points on the eyelid and canthi;

automatically segmenting an eye-region from the facial image of the subject by identifying eyes from the facial image based on the position of the plurality of the facial landmarks;

automatically determining a position of the eyelid by estimating the eyelid shape curve in the segmented eye region, wherein the eyelid shape curve refers to a contour of a junction of the eyelid with the eye;

automatically determining a red reflex in iris of the eye by processing the segmented eye region;

measuring a refractive error by automatically identifying the red reflex with a reddish hue and a crescent in the iris, wherein the refractive error is measured by thresholding the red reflex images using a red channel of the RGB image and calculating an average red value as a threshold value;

automatically generating a mask of the crescent by thresholding the red reflex image using an Otsu's binary thresholding technique, wherein the crescent comprises a segment of a circular pupil;

automatically determining a width of anti-crescent in the red reflex image using a number of white pixels in the mask;

automatically determining a spherical power using the width of the anti-crescent, eccentricity of the image capturing device, a working distance of the image capturing device and a diameter of the pupil.

18. The one or more non-transitory computer readable storage mediums storing instructions as claimed in claim 17, wherein automatic determination of the red reflex in the iris of the eye comprising the steps of:

automatically estimating an average lightness value of all the pixels in an eye bounding box associated with the iris of the eye;

automatically identifying a plurality of iris shades in the eye by classifying an angle representing hue, wherein the angle representing hue is classified by comparing against various thresholds;

automatically segmenting, using a sliding-window algorithm, the iris as the region with the highest concentration of dark-colored pixels, wherein the dark-colored pixels are determined based on the estimated average lightness value of the pixels; and automatically trimming the iris region of the image based on the red channel in the eye to obtain the red reflex image of the iris.

19. A system for automatically analyzing an image of the face of the subject containing the red reflex (or retinoscopic reflex) associated with the image, measuring a refractive error associated with eyes of a subject, and determining a spherical power of the eyes of the subject based on the measured refractive error associated with the red reflex image for detecting optical imperfection conditions, the system comprising:

a memory that stores a database (201);
a device processor that is configured to
generate a database with a facial image associated with a subject, wherein the facial image is captured using an image capturing device;

predict a position of a plurality of facial landmarks on the facial image of the subject including points on the eyelid and canthi, by implementing an ensemble of regression trees model using a facial landmark detection technique;

segment an eye region from the facial image of the subject by identifying the eyes from the facial image based on the position of the plurality of the facial landmarks;

determine a position of the eyelid by estimating the eyelid shape curve in the segmented eye region, wherein the eyelid shape curve refers to a contour of a junction of the eyelid with the eye;

determine a red reflex in iris of the eye by processing the segmented eye region;

automatically identify the red reflex with a reddish hue and a crescent in the iris, wherein the refractive error is measured by thresholding the red reflex images using a red channel of the RGB image and calculating an average red value as threshold value;

generate a mask of the crescent by thresholding the red reflex image using an Otsu's binary thresholding technique, wherein the crescent comprises a segment of a circular pupil;

determine a width of anti-crescent in the red reflex image using a number of white pixels in the mask; and determine a spherical power using the width of the anti-crescent, eccentricity of the image capturing device, a working distance of the image capturing device and a diameter of the pupil.

20. The system as claimed in claim 19, wherein the device processor is configured to determine the red reflex in the iris of the eye by:

automatically estimating an average lightness value of all the pixels in an eye bounding box associated with the iris of the eye;

automatically identifying a plurality of iris shades in the eye by classifying an angle representing hue, wherein the angle representing hue is classified by comparing against various thresholds;

automatically segmenting, using a sliding-window algorithm, the iris as the region with the highest concentration of dark-colored pixels, wherein the dark-colored pixels are determined based on the estimated average lightness value of the pixels; and automatically trimming the iris region of the image based on the red channel in the eye to obtain the red reflex image of the iris.

* * * * *